United States Patent [19]

Weiguny et al.

[11] Patent Number: 5,789,593

[45] Date of Patent: Aug. 4, 1998

[54] PROCESS FOR PREPARING INDENES

[75] Inventors: Jens Weiguny, Freinsheim; Holger Borchert, Frankfurt; Uwe Dingerdissen, Seeheim-Jugenheim, all of Germany

[73] Assignee: Targar GmbH, Germany

[21] Appl. No.: 812,428

[22] Filed: Mar. 6, 1997

[30] Foreign Application Priority Data

Mar. 7, 1996 [DE] Germany ............... 196 08 814.3

[51] Int. Cl.$^6$ .................................................. C07D 221/02
[52] U.S. Cl. .................. 546/112; 585/411; 502/329; 556/465
[58] Field of Search ................. 585/411; 502/324, 502/327, 329, 342, 344, 345, 349; 546/112; 556/465

[56] References Cited

U.S. PATENT DOCUMENTS

| 4,892,851 | 1/1990 | Ewen et al. . |
| 4,931,417 | 6/1990 | Miya et al. . |
| 4,962,262 | 10/1990 | Winter et al. . |
| 5,324,800 | 6/1994 | Welborn, Jr. et al. . |
| 5,504,172 | 4/1996 | Imuta ........................... 526/351 |

FOREIGN PATENT DOCUMENTS

| 1319784 | 6/1993 | Canada . |
| 0 129 368 | 12/1984 | European Pat. Off. . |
| 0 316 155 | 5/1989 | European Pat. Off. . |
| 0 321 852 | 6/1989 | European Pat. Off. . |
| 0 336 128 | 10/1989 | European Pat. Off. . |
| 0 351 392 | 1/1990 | European Pat. Off. . |

OTHER PUBLICATIONS

CA:106:175986, abstra of Reaction of flavin analogs and other heterocycles as model for bacterial bioluminesence, Tetrahedron .42(12), 322–43, Mc Capra 1986.

Spaleck et al, *New J. Chem.*, "Stereorigid Metallocenes: Correlations Between Structure and Behaviour in Homopolymerizations of Propylene", 1990, 14, pp. 499–503.

Piccoirovazzi et al, *Organomet.* "Electronic Effects in Homogeneous Indenylzirconium Ziegler–Natta Catalysts", 1990, 9, pp. 3098–3105.

Von Werner Roll et al, *Angew. Chem.*, "Stereo– und Regioselektivitat von chiralen, alkylsubstituierten ansa–Zircononocen–Katalysatoren bei der Methylalumoxan–aktivierten Propen–Polymerisation", 1990, 102, pp. 339–342.

John D. Prugh et al, *J. Med. Chem.*, "3–Hydroxy–3–methylglutaryl–coenzyme A Reductase Inhibitors", 1990, 33, pp. 758–765.

Maurice Olivier et al, *Bulletin De La Societe*, "Etude de monomeres halogenes et de leur polymersation cationizue", France, 1973, 11, pp. 3092–3094.

Claude Normant–Chefnay, *Bull. Soc. Chim. France*, "Recherches dans la serie de lhomoisochromanne", 1971, pp. 1351–1362.

Calvin L. Becker et al, *Letters Synlett* "Improved Syntheses of 1 H–benz[f]indene", 1991, 9, p. 642.

Nynke M. Spijker et al, *J. Org. Chem.*, "A Very Convenient Synthesis of Cyclopenta[cd]pyrene", 1990, 55, pp. 756–758.

Derek R. Buckle et al, *J. Med. Chem.*, "Synthesis and Smooth Muscle Relaxant Activity of a New Series of Potassium Channel Activators: 3–Amido–1, 1–dimethylindan–2–ols", 1991, 34, pp. 919–926.

*Primary Examiner*—Alan L. Rotman
*Assistant Examiner*—Jean F. Vollano
*Attorney, Agent, or Firm*—Connolly & Hutz

[57] ABSTRACT

The present invention relates to a process for preparing an indene, which involves reacting an indanone with hydrogen in the presence of a catalyst comprising one or more oxides, preferably metal oxides. Preferred oxides comprise elements from groups Ia, IIa, IIIa, IVa, Va, VIa, Ib, IIb, IIIb, IVb, Vb, VIb, VIIb and VIII of the Periodic Table, or elements from the lanthanide group.

13 Claims, No Drawings

PROCESS FOR PREPARING INDENES

The present invention relates to a technically simple process for preparing indenes in the presence of oxide catalysts, especially metal oxide catalysts.

Indenes are important intermediates in the production of metallocene complexes, indenes being used as a ligand system for the synthesis of metallocene complexes (EP-A 336 128). Bridged, chiral bis-indenyl-zirconocenes in particular are of great importance as high-activity catalysts in the polymerization of olefins (cf. EP-A 129 368; EP-A 321 852). By varying the ligand system, for instance by substitution, it is possible to exert controlled influence over the catalyst properties. By this means it is possible to alter the polymer yields, molar mass, tacticity or melting point of the polymers to the desired extent (New J. Chem. 1990, 14, 499; Organomet. 1990, 9, 3098; Angew. Chem. 1990,102, 339; EP-A 316 155; EP-A 351 392).

The literature includes descriptions of processes for preparing substituted indenes from the corresponding indanones. In one such process, an indanone is first of all reduced to the corresponding alcohol using a reducing agent such as $NaBH_4$ (J. Med. Chem. 1990, 33, 758), $LiAlH_4$ (Bull. Soc. Chim. Fr. 1973, 11, 3092) or $KBH_4$ (J. Med. Chem. 1991, 34, 919). This reduction can also be carried out using the method of Meerwein-Ponndorf-Verley with Al(i-Pr)$_3$ (Bull. Soc. Chim. Fr. 1971, 1351). In some cases it is also possible to carry out hydrogenation with hydrogen over a Raney nickel catalyst. However, 2-methylindene, for example, cannot be reacted at all (Houben Weyl 4/1c p. 205). The alcohol is then converted to the indene in a second step by elimination of water. To do this requires acidic catalysts such as acetic acid (J. Org. Chem. 1992, 57, 2), p-toluenesulfonic acid (Organomet. 1990, 9, 3098), HCl (Bull. Soc. Chim. Fr. 1971, 1351), $H_2SO_4$ (Synlett 1991, 9, 642) or $KHSO_4$ (Bull. Soc. Chim. Fr. 1973, 11, 3092). As an alternative to acidic catalysts it is also possible to employ dehydrating agents such as $P_2O_5$ (J. Med. Chem. 1991, 34, 919).

In another process, the indanone is converted to the corresponding indane in a Wolff-Kizner reduction using hydrazine in the presence of sodium alcoholate. This indane is then dehydrogenated to give the indene in a second step using 2,3-dichloro-5,6-dicyano-p-benzoquinone (DDQ) (J. Org. Chem. 1990, 55, 756).

The processes of the prior art have the disadvantage that they involve two stages and are therefore highly laborious. Moreover, the first-mentioned process uses expensive reagents such as $NaBH_4$ or $LiAlH_4$ in excess, which leads in turn to a considerable production of waste. The subsequent dehydration is hampered by the problem that, as a result of the elevated temperature and the acidic catalyst, polymerization may occur, or that it is necessary to use dehydrating agents. In the second process mentioned, reduction is carried out using toxic hydrazine, and dehydrogenation using equimolar amounts of toxic and expensive DDQ.

The object was therefore to find a process for preparing indenes which avoids the disadvantages known from the prior art.

It has now surprisingly been found that indanones can be converted with hydrogen into indenes in one reaction step over an oxide catalyst.

The present invention therefore provides a process for preparing an indene, which involves reacting an indanone with hydrogen in the presence of a catalyst comprising one or more oxides, especially metal oxides.

Preferred oxides are those of elements from groups Ia, IIa, IIIa, IVa, Va, VIa, Ib, IIb, IIIb, IVb, Vb, VIb, VIIb and VIII of the Periodic Table of the Elements, or oxides of the elements from the lanthanide group. Preferred catalysts are oxides, especially metal oxides of the formula (I)

$$Zn_aM^1_bM^2_cO_x \qquad (I)$$

in which $M^1$ is at least one element from the group consisting of aluminum, zirconium, titanium and silicon and $M^2$ is at least one element from the group consisting of cadmium, copper, silver, nickel, cobalt, iron, manganese, chromium, molybdenum, tantalum, scandium, tungsten, vanadium, niobium, hafnium, yttrium, boron, indium, tin, lead, bismuth, selenium, gallium, germanium, antimony, arsenic, tellurium or a lanthanide element, a is 1, b is from 0 to 20, preferably from 0.01 to 20, particularly preferably from 0.1 to 10, and c is from 0 to 3, preferably from 0.01 to 2, and x has a value which results from the stoichiometry and from the oxidation states of the metals Zn, $M^1$ and $M^2$.

The letters a, b, c and x indicate the atomic ratio of the respective elements. a, b, c and x can take on identical or different values. Examples of oxides of the formula (I) are $ZnO$, $Zn_aAl_bO_x$, $Zn_aAl_bCo_cO_x$, $Zn_aAl_bNi_cO_x$, $Zn_aAl_bCe_cO_x$, $Zn_a(AlSi)_bO_x$, $Zn_a(AlTi)_bO_x$, $Zn_a(AlZr)_bO_x$, where preferably a=1, $1 \leq b \leq 3$, $0.01 \leq c \leq 0.1$ and x results from the stoichiometry and from the oxidation states of the metals.

In a further preferred embodiment of the present invention it is possible, instead of oxides of the formula (I), to employ oxides of the formula (II)

$$M^3_2M^4O_4 \qquad (II)$$

which are double oxides from the class of the spinel compounds (Chemie der Elemente, N. N. Greenwood, A. Earnshaw, VCH-Verlagsgesellschaft mbH, Weinheim, 1990; Lehrbuch der Anorganischen Chemie, A. F. Holleman, N. Wiberg, de Gruyter, Berlin, 1985). In formula (II), $M^3$ and $M^4$ can be any desired element from the Periodic Table of the Elements, $M^3$ being an element with the oxidation state I, II or III and $M^4$ being an element with the oxidation state II, III VI. It is preferred that, if $M^3$ is an element with the oxidation state I, $M^4$ has the oxidation state VI; if $M^3$ is an element with the oxidation state II, $M^4$ has the oxidation state IV; and, if $M^3$ is an element with the oxidation state III, $M^4$ has the oxidation state II. It is also possible for $M^3$ and $M^4$ to be the same element, provided it is able to exist in the appropriate, different oxidation states. Examples of oxides of the formula (II) are $Al_2ZnO_4$, $Al_2CoO_4$, $Al_2MnO_4$, $Al_2FeO_4$, $Al_2NiO_4$ and $Cr_2FeO_4$.

The catalyst employed in accordance with the invention can be prepared by impregnation of supports and shaped articles or by coprecipitation and subsequent drying and calcination. A further possibility is that of direct calcination of appropriate metal compounds, for example of nitrates, acetates, carbonates or other salts and complexes of the elements $M^1$ to $M^4$.

For impregnation on supports, a solution of compounds of the elements $M^1$ to $M^4$ can be applied to a support, which is preferably inorganic and can consist, for example, of $SiO_2$, SiC, $Al_2O_3$, $Al(OH)_3$, $ZrO_2$, alumosilicates, SiN or $TiO_2$. Examples of compounds of the elements $M^1$ to $M^4$ suitable for impregnation are their halides, nitrates, sulfates, oxalates, carboxylates and alkoxides. The impregnated supports are subsequently dried at from 100° C. to 150° C., preferably at 130° C., and are calcined at 400°–1000° C., preferably at from 500° to 800° C. The catalysts prepared in this way can be processed further by customary techniques, before or after being calcined to form pellets, tablets or extrudates.

For coprecipitation, suitable compounds of the elements $M^1$ to $M^4$ can be precipitated at appropriate pH levels. Following precipitation, resulting hydroxides are filtered off and washed with an appropriate solvent. Drying takes place at from 100° to 150° C., preferably at 130° C., with or without application of a vacuum, and calcination is carried out at from 400° to 1000° C., preferably at from 500° to 900° C. The catalyst prepared in this way is present in granule form and, following its comminution to the desired particle size, can be employed directly in the reaction.

Before its use in the novel process, the catalyst can be prefinished at temperatures from 100° to 800° C. using an appropriate reducing agent. The novel process can be carried out continuously or batchwise in an appropriate reactor. It has proven expedient to operate at a temperature of from 200° to 600° C., in particular at from 250° to 400° C., and under a pressure of from 0.1 to 10 bar, in particular at atmospheric pressure.

The novel process can be conducted with molecular hydrogen, which can also be prepared in situ. Another possibility is to dilute the hydrogen with an inert gas such as nitrogen or argon. The indanone employed in accordance with the invention can be used in the form of a solid, melt, liquid or solution in an appropriate solvent, such as benzene, xylene, toluene or cyclohexane. The indanone is preferably supplied to an evaporator and then, in the gas phase, brought into contact with the catalyst employed in accordance with the invention. The molar ratio of indanone to hydrogen is preferably from 1:1 to 1:500, particularly preferably from 1:2 to 1:50. The feed rate for the indanones is preferably from 0.01 to 20 $g/ml_{catalyst} \cdot h$ (LHSV: liquid hourly space velocity), particularly preferably from 0.2 to 5 $g/ml_{catalyst} \cdot h$. The feed rate of the hydrogen is preferably from 50 to 50,000 $h^{-1}$ (GHSV: gaseous hourly space velocity), particularly preferably from 100 to 10,000 $h^{-1}$.

The novel process is preferably carried out using an indanone of the formula (III)

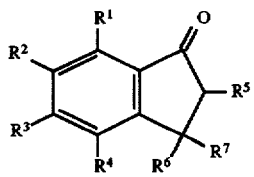

(III)

in which $R^1$, $R^2$, $R^3$, $R^4$, $R^5$, $R^6$ and $R^7$ are identical or different and are a hydrogen atom, a halogen atom or a $C_1-C_{30}$ carbon-containing radical such as $(C_1-C_{20})$-alkyl, $(C_6-C_{14})$-aryl, $(C_1-C_{10})$-alkoxy, $(C_2-C_{10})$-alkenyl, $(C_7-C_{20})$-arylalkyl, $(C_7-C_{20})$-alkylaryl, $(C_6-C_{10})$-aryloxy, $(C_1-C_{10})$-fluoroalkyl, $(C_6-C_{10})$-haloaryl, $(C_2-C_{10})$-alkynyl or $-SiR^8_3$, in which $R^8$ is $(C_1-C_{10})$-alkyl, or two or more radicals $R^1$ to $R^7$ are able, with the atoms connecting them, to form one or more substituted or unsubstituted rings. The $C_1-C_{30}$ carbon-containing radical can be a heteroaromatic radical, preferably having 5 or 6 ring members, which can contain one or more heteroatoms such as nitrogen, phosphorus or sulfur.

Alkyl is straight-chain, cyclic or branched alkyl. Halogen is fluorine, chlorine, bromine or iodine, especially fluorine or chlorine. Examples of heteroaromatic radicals are thienyl, furyl and pyridyl.

The rings formed by adjacent radicals $R^1$ to $R^7$ can be substituted by substituents in the definition of $R^1$ to $R^7$, including the ranges of preference indicated for these radicals.

In the formula (III), preferably, $R^1$, $R^2$, $R^3$ and $R^4$ are identical or different and are hydrogen, $(C_6-C_{10})$-aryl or $(C_1-C_{10})$-alkyl, or the radicals $R^1$ and $R^2$, $R^2$ and $R^3$ or $R^3$ and $R^4$, with the atoms connecting them, form a substituted or unsubstituted six-membered, saturated or unsaturated carbocycle, $R^5$ is methyl, and $R^6$ and $R^7$ are hydrogen.

The saturated or unsaturated five- or six-membered ring (carbocycle) formed by adjacent substituents $R^1-R^4$ may additionally carry substituents, preferably $(C_1-C_{10})$-alkyl.

The novel process is preferably used to prepare an indene of the formula (IV) or its isomers (Va) and (Vb)

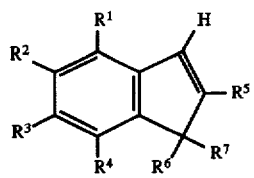

(IV)

in which $R^1$, $R^2$, $R^3$, $R^4$, $R^5$, $R^6$ and $R^7$ are identical or different and are a hydrogen atom, a halogen atom or a $C_1-C_{30}$ carbon-containing radical such as $(C_1-C_{20})$-alkyl, $(C_6-C_{14})$-aryl, $(C_1-C_{10})$-alkoxy, $(C_2-C_{10})$-alkenyl, $(C_7-C_{20})$-arylalkyl, $(C_7-C_{20})$-alkylaryl, $(C_6-C_{10})$-aryloxy, $(C_1-C_{10})$-fluoroalkyl, $(C_6-C_{10})$-haloaryl, $(C_2-C_{10})$-alkynyl or $-SiR^8_3$, in which $R^8$ is $(C_1-C_{10})$-alkyl, or two or more radicals $R^1$ to $R^7$ are able, with the atoms connecting them, to form one or more substituted or unsubstituted rings. The $C_1-C_{30}$ carbon-containing radical can be a heteroaromatic radical, preferably having 5 or 6 ring members, which can contain one or more heteroatoms such as nitrogen, phosphorus or sulfur.

Alkyl is straight-chain, cyclic or branched alkyl. Halogen is fluorine, chlorine, bromine or iodine, especially fluorine or chlorine. Examples of heteroaromatic radicals are thienyl, furyl and pyridyl.

The rings formed by adjacent radicals $R^1$ to $R^7$ can be substituted by substituents in the definition of $R^1$ to $R^7$, including the ranges of preference indicated for these radicals.

In the formula (IV), preferably, $R^1$, $R^2$, $R^3$ and $R^4$ are identical or different and are hydrogen, $(C_6-C_{10})$-aryl or $(C_1-C_{10})$-alkyl, or the radicals $R^1$ and $R^2$, $R^2$ and $R^3$ or $R^3$ and $R^4$, with the atoms connecting them, form a substituted or unsubstituted six-membered, saturated or unsaturated carbocycle, $R^5$ is methyl, and $R^6$ and $R^7$ are hydrogen.

The saturated or unsaturated five- or six-membered ring (carbocycle) formed by adjacent substituents $R^1-R^4$ may additionally carry substituents, preferably $(C_1-C_{10})$-alkyl.

Examples of indenes of the formula (IV) are indene, 2-methylindene, 3-methylindene, 3-tert-butylindene, 3-trimethylsilylindene, 2-methyl-4-phenylindene, 2-methyl-4-(2'-pyridyindene, 2-ethyl-4-phenylindene, 2-methyl-naphthylindene, 2-methyl-4-isopropylindene, 2-methyl-4,6-diisopropylindene, benzoindene, 2-methyl-4,5-benzoindene, 2-methyl-acenaphthindene, 2-ethyl-naphthylindene and 2-ethyl-4-isopropylindene.

The indene of the formula (IV) has a double-bond isomer, which itself has two constitutional isomers (formulae Va and Vb).

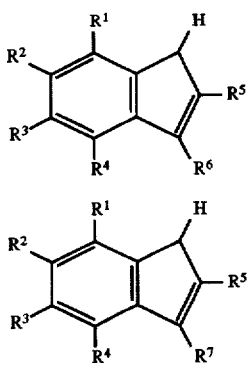

(Va)

(Vb)

The indenes prepared by the novel process can be purified to remove by-products by distillation, column chromatography or crystallization. The isomers obtained can as a mixture be employed directly for the synthesis of the corresponding metallocene complexes. The synthesis of such metallocenes starting from indenes is described, for example, in AU-A-31479/89; J. Organomet. Chem. 1988, 342, 21 and EP-A 284 707.

Features of the novel process are that it is technically simple to carry out and delivers the desired indenes with very good selectivities, preferably with selectivities from 89 to 99.9%, particularly preferably with selectivities from 95 to 99%.

The purpose of the Examples below is to illustrate the present invention; however, they have no limiting character whatsoever.

EXAMPLE A 139.0 g of $Al(NO_3)_3 \times 9$ $H_2O$ and 55.0 g of $Zn(NO_3)_2 \times 6$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE B 69.5 g of $Al(NO_3)_3 \times 9$ $H_2O$ and 110.0 g of $Zn(NO_3)_2 \times 6$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE C 139.0 g of $Al(NO_3)_3 \times 9$ $H_2O$ and 110.0 g of $Zn(NO_3)_2 \times 6$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE D 139.0 g of $Al(N_3)_3 \times 9$ $H_2O$ and 54.9 g of $Zn(NO_3)_2 \times 6$ $H_2O$ and 2.2 g of $Co(NO_3)_3 \times 9$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE E 139.0 g of $Al(NO_3)_3 \times 9$ $H_2O$ and 54.9 g of $Zn(NO_3)_2 \times 6$ $H_2O$ and 1.35 g of $Cu(NO_3)_2 \times 3$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE F 139.0 g of $Al(NO_3)_3 \times 9$ $H_2O$ and 54.9 g of $Zn(NO_3)_2 \times 6$ $H_2O$ and 2.23 g of $Cr(NO_3)_3 \times 9$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE G 139.0 g of $Al(NO_3)_3 \times 9$ $H_2O$ and 54.9 g of $Zn(NO_3)_2 \times 6$ $H_2O$ and 1.62 g of $Ni(NO_3)_2 \times 6$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE H 139.0 g of $Al(NO_3)_3 \times 9$ $H_2O$ and 54.9 g of $Zn(NO_3)_2 \times 6$ $H_2O$ and 1.40 g of $Mn(NO_3)_2 \times 4$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE I 139.0 g of $Al(NO_3)_3 \times 9$ $H_2O$ and 54.9 g of $Zn(NO_3)_2 \times 6$ $H_2O$ and 2.03 g of $Y(NO_3)_3 \times 6$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE J 139.0 g of $Al(NO_3)_3 \times 9$ $H_2O$ and 54.9 g of $Zn(NO_3)_2 \times 6$ $H_2O$ and 2.25 g of $Fe(NO_3)_3 \times 9$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE K 139.0 g of $Al(NO_3)_3 \times 9$ $H_2O$ and 54.9 g of $Zn(NO_3)_2 \times 6$ $H_2O$ and 2.42 g of $Ce(NO_3)_3 \times 6$ $H_2O$ are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLE L 139.0 g of Al(NO$_3$)$_3$×9 H$_2$O and 54.9 g of Zn(NO$_3$)$_2$×6 H$_2$O and 1.16 g of tetraethoxysilane are dissolved in 3.8 l of water, and the solution is cooled to 5° C. and adjusted to a pH of 9 using 25% strength ammonia solution. The precipitate is filtered off and washed with water, dried at 130° C. and calcined at 600° C. Following comminution to particle sizes from 10 to 20 mesh, the catalyst is prefinished in a stream of hydrogen at 450° C.

EXAMPLES 1–13

2-Methylindanone was converted to 2-methylindene in a tubular reactor using hydrogen in the presence of the catalysts from Examples A–L (Examples 1–12) or in the presence of a ZnO catalyst (Example 13). The bulk volume of the catalyst employed was 20 ml. The 2-methylindanone employed was evaporated in an upstream evaporator. GHSV, LHSV and reaction temperature are indicated in Table 1. The reaction product was passed through a condenser and analyzed by gas chromatography.

TABLE 1

| Ex. | Catalyst from Example | GHSV [h$^{-1}$] | LHSV [g/ml$_{cat}$h] | Temperature | Conversion | Selectivity |
|---|---|---|---|---|---|---|
| 1 | A | 1250.00 | 0.61 | 350° C. | 100% | 98% |
| 2 | B | 1250.00 | 0.20 | 350° C. | 100% | 95% |
| 3 | C | 1250.00 | 0.38 | 350° C. | 100% | 95% |
| 4 | D | 1250.00 | 0.38 | 310° C. | 100% | 99% |
| 5 | E | 1250.00 | 0.38 | 330° C. | 97% | 92% |
| 6 | F | 1250.00 | 0.38 | 330° C. | 98% | 92% |
| 7 | G | 1250.00 | 0.38 | 310° C. | 100% | 99% |
| 8 | H | 1250.00 | 0.38 | 350° C. | 100% | 92% |
| 9 | I | 1250.00 | 0.38 | 350° C. | 100% | 89% |
| 10 | J | 1250.00 | 0.38 | 310° C. | 97% | 93% |
| 11 | K | 1250.00 | 0.38 | 310° C. | 100% | 99% |
| 12 | L | 1250.00 | 0.38 | 310° C. | 99% | 94% |
| 13 | ZnO catalyst | 1250.00 | 0.38 | 330° C. | 100% | 99% |

We claim:

1. A process for preparing an indene, which comprises reacting an indanone with hydrogen in the presence of a catalyst comprising one or more oxides.

2. The process as claimed in claim 1, wherein the oxide comprises an element of groups Ia, IIa, IIIa, IVa, Va, VIa, Ib, IIb, IIIb, IVb, Vb, VIb, VIIb or VIII of the Periodic Table of the Elements, or an element from the lanthanide group.

3. The process as claimed in claim 1, wherein the oxide is a compound of the formula (I)

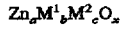

(I)

in which M$^1$ is at least one element from the group consisting of aluminum, zirconium, titanium and silicon and M$^2$ is at least one element from the group consisting of cadmium, copper, silver, nickel, cobalt, iron, manganese, chromium, molybdenum, tantalum, scandium, tungsten, vanadium, niobium, hafnium, yttrium, boron, indium, tin, lead, bismuth, selenium, gallium, germanium, antimony, arsenic, tellurium and a lanthanide element, a is 1, b is from 0.01 to 20, and c is from 0 to 3, and x has a value which results from the stoichiometry and from the oxidation states of the metals Zn, M$^1$ and M$^2$.

4. The process as claimed in claim 1, wherein the oxide is a compound of the formula (II)

(II)

in which M$^3$ is a metal element with the oxidation state I, II or III and M$^4$ is a metal element with the oxidation state II, III or VI.

5. The process as claimed in claim 4, wherein in formula II, if M$^3$ is an element with the oxidation state I, M$^4$ has the oxidation state VI; if M$^3$ is an element with the oxidation state II, M$^4$ has the oxidation state IV; and, if M$^3$ is an element with the oxidation state III, M$^4$ has the oxidation state II.

6. The process as claimed in claim 1, in which an indanone of the formula (III) is employed

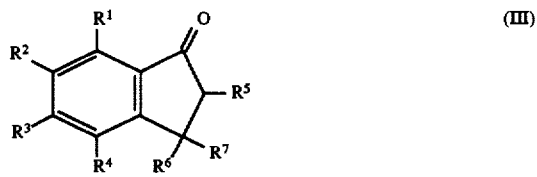

(III)

in which R$^1$, R$^2$, R$^3$, R$^4$, R$^5$, R$^6$ and R$^7$ are identical or different and are a hydrogen atom, a halogen atom or a C$_1$–C$_{30}$ carbon-containing radical which can optionally contain one or more heteroatoms, or two or more radicals R$^1$ to R$^7$ are able, with the atoms connecting them, to form one or more substituted or unsubstituted rings.

7. The process as claimed in claim 1, wherein said oxides are metal oxides.

8. The process as claimed in claim 3, wherein b is from 0.1 to 10 and c is from 0.01 to 2.

9. The process as claimed in claim 4, wherein the oxide of the formula (II) is selected from the group consisting of Al$_2$ZnO$_4$, Al$_2$CoO$_4$, Al$_2$MnO$_4$, Al$_2$FeO$_4$, Al$_2$NiO$_4$ and Cr$_2$FeO$_4$.

10. The process as claimed in claim 6, wherein R$^1$, R$^2$ R$^3$, R$^4$, R$^5$, R$^6$ and R$^7$ are identical or different and are a hydrogen atom, a halogen atom (C$_1$–C$_{20}$)-alkyl, (C$_6$–C$_{14}$)-aryl, (C$_1$–C$_{10}$)-alkoxy, (C$_2$–C$_{10}$)-alkenyl, (C$_7$–C$_{20}$)-arylalkyl, (C$_7$–C$_{20}$)-alkylaryl, (C$_6$–C$_{10}$)-aryloxy, (C$_1$–C$_{10}$)-fluoroalkyl, (C$_6$–C$_{10}$)-haloaryl, (C$_2$–C$_{10}$)-alkynyl or —SiR$^8$$_3$, in which R$^8$ is (C$_1$–C$_{10}$)-alkyl, or two or more radicals R$^1$ to R$^7$ are able, with the atoms connecting them, to form one or more substituted or unsubstituted rings.

11. The process as claimed in claim 6, wherein said C$_1$ to C$_{30}$ carbon containing radical is substituted by one or more heteroatoms, said heteroatoms are selected from the group consisting of nitrogen, phosphorus and sulfur.

12. The process as claimed in claim 10, wherein R$^1$, R$^2$, R$^3$ and R$^4$ are identical or different and are hydrogen, (C$_6$–C$_{10}$)-aryl or (C$_1$–C$_{10}$)-alkyl, or the radicals R$^1$ and R$^2$, R$^2$ and R$^3$ or R$^3$ and R$^4$, with the atoms connecting them, form a substituted or unsubstituted six-membered, saturated or unsaturated carbocycle, R$^5$ is methyl, and R$^6$ and R$^7$ are hydrogen.

13. The process as claimed in claim 3, wherein the oxide of formula 1 is selected from the group consisting of ZnO, Zn$_a$Al$_b$O$_x$, Zn$_a$Al$_b$Co$_c$O$_x$, Zn$_a$Al$_b$Ni$_c$O$_x$, Zn$_a$Al$_b$Ce$_c$O$_x$, Zn$_a$(AlSi)$_b$O$_x$, Zn$_a$(AlTi)$_b$O$_x$ and Zn$_a$(AlZr)$_b$O$_x$ where a=1, 1≦b≦3, 0.01≦c≦0.1.

* * * * *